(12) United States Patent
Mantyla et al.

(10) Patent No.: US 7,155,356 B2
(45) Date of Patent: Dec. 26, 2006

(54) QUALITY AND CONDITION MONITORING BASED ON SPECTRUM SEPARATING MEASUREMENT

(75) Inventors: Markku Mantyla, Kangasala (FI); Matti Kukkurainen, Tampere (FI); Antti Komulainen, Keuruu (FI)

(73) Assignee: Metso Automation Oy, Helsinki (FI)

( * ) Notice: Subject to any disclaimer, the term of this patent is extended or adjusted under 35 U.S.C. 154(b) by 40 days.

(21) Appl. No.: 10/497,188

(22) PCT Filed: Nov. 29, 2002

(86) PCT No.: PCT/FI02/00966

§ 371 (c)(1),
(2), (4) Date: Sep. 2, 2004

(87) PCT Pub. No.: WO03/046529

PCT Pub. Date: Jun. 5, 2003

(65) Prior Publication Data

US 2005/0021262 A1  Jan. 27, 2005

(30) Foreign Application Priority Data

Nov. 29, 2001 (FI) .................................. 20012335

(51) Int. Cl.
*G01N 21/86* (2006.01)

(52) U.S. Cl. ............................ 702/76; 702/81; 702/84; 702/183; 250/559.01; 250/559.42

(58) Field of Classification Search ................ 702/76, 702/33–36, 40, 79, 81–84, 105, 113–115, 702/56, 66, 127, 124, 182–185, 188, 189; 162/198, 263, 252, 262, 265, 272, 253, 259, 162/DIG. 10, 100, DIG. 11, 49, DIG. 6; 250/341.7, 341.8, 559.01, 559.04, 339.1, 250/339.11, 554.05, 559.42, 359.1, 339.01, 250/339.07, 340

See application file for complete search history.

(56) References Cited

U.S. PATENT DOCUMENTS

| 3,641,349 A | 2/1972 | Dahlin | 250/350 |
| 4,733,078 A | 3/1988 | Sturm | 250/339.1 |

(Continued)

FOREIGN PATENT DOCUMENTS

FI  902034  10/1991

(Continued)

OTHER PUBLICATIONS

Chen et al., "Control Systems '98, Information tools to match the evolving operator role," Sep. 1-3, 1998, Porvoo, Finland, pp. 330-337.

*Primary Examiner*—Hal D. Wachsman
(74) *Attorney, Agent, or Firm*—Oliff & Berridge, PLC

(57) ABSTRACT

A method of controlling the quality and/or condition of a fibre web in a process for manufacturing and/or finishing the fibre web, which includes, monitoring the fibre web with at least one optical spectrum separating measurement device, determining a quality variable of the fibre web, measuring electromagnetic radiation reflected from the fibre web using an optical spectrum separating measurement device synchronously with a movement of the fibre web, and measurements in the form of spectral data, generating a continuous quality variable chart, dividing the continuous quality variable chart into successive matched partial charts having a cycle length, detecting deviations and/or discontinuities of the quality variable from the successive matched partial charts, and detecting malfunctioning of a rotating/moving means using the detected deviations and/or discontinuities of the quality variable.

16 Claims, 5 Drawing Sheets

U.S. PATENT DOCUMENTS

| | | | |
|---|---|---|---|
| 4,801,809 A | 1/1989 | Burk et al. | 250/559.04 |
| 5,019,710 A | 5/1991 | Wennerberg et al. | 250/341.7 |
| 5,358,606 A | 10/1994 | Makkonen | 162/49 |
| 5,533,145 A | 7/1996 | Shofner et al. | 382/141 |
| 5,696,591 A | 12/1997 | Bilhorn et al. | 356/429 |
| 5,960,374 A | 9/1999 | Lausier | 702/81 |
| 6,179,964 B1* | 1/2001 | Begemann et al. | 162/198 |
| 6,187,145 B1* | 2/2001 | Furumoto et al. | 162/198 |
| 6,188,077 B1* | 2/2001 | Lind | 250/559.01 |
| 6,411,860 B1* | 6/2002 | Chen | 700/129 |
| 6,495,831 B1* | 12/2002 | Hyvarinen et al. | 250/339.07 |
| 2002/0085201 A1* | 7/2002 | Shakespeare et al. | 356/429 |
| 2002/0166970 A1* | 11/2002 | Komulainen et al. | 250/340 |
| 2003/0222219 A1* | 12/2003 | Almi et al. | 250/341.2 |

FOREIGN PATENT DOCUMENTS

| | | |
|---|---|---|
| WO | WO 99/02941 | 1/1999 |
| WO | WO 99/10833 | 3/1999 |
| WO | WO 99/14579 | 3/1999 |
| WO | WO 99/28730 | 6/1999 |
| WO | WO 00/31521 | 6/2000 |
| WO | WO 00/45156 | 8/2000 |
| WO | WO 01/48462 A1 | 7/2001 |

* cited by examiner

QUALITY AND CONDITION MONITORING BASED ON SPECTRUM SEPARATING MEASUREMENT

FIELD OF THE INVENTION

The invention relates to a method for controlling quality and condition on the basis of spectrum separating measurement, to be used in connection with processes of manufacturing or finishing a continuous fibre web, particularly a paper web.

BACKGROUND OF THE INVENTION AND PRIOR ART

In the manufacturing and finishing processes of paper, paperboard and other corresponding web-like materials, the significance of methods and systems monitoring the web as such and/or the process in real time increases continuously when the aim is to achieve as high a production capacity as possible and a high and equal quality of the product.

The use of optical methods has been found to be very efficient in implementing real-time monitoring of a rapidly moving fibre web and its path. Advantages of optical methods include, for example, the possibility to perform measurements of the object in a contactless manner and to perform measurements with a rapid time response. Several examples of applying optical methods in the manufacturing and finishing processes of web-like materials are known from prior art.

In so-called imaging methods, i.e. methods which produce a visual image of an object and which are known from prior art, the object is typically recorded with matrix or line scan cameras, which are based on CCD technology (Charged Coupled Device) and thus operate on a substantially visible wavelength range. Imaging measurements may be performed as local measurements, but nowadays also as measurements monitoring the fibre web across its entire production width. Prior art is described, for example, in the conference publication "Paper Machine Applications with Fullsheet Imaging Measurement" (Chen Shih-Chin et al, Control Systems '98: Information tools to match the evolving operator role, pages 330 to 337, Porvoo, Finland, Sep. 1 to 3, 1998). In imaging measurements, the user aims at recognizing visually detectable abnormal phenomena and their causes in the object from the image either by him/herself or with the help of computer image processing.

In addition to the imaging diagnostics, which operates on the visible range, prior art also recognizes the use of thermal cameras operating in the infrared range for monitoring the fibre web and its path.

Prior art further recognizes optical methods based on spectral separation as well, wherein the characteristics of the object, e.g. paper web, are determined quantitatively by measuring and analysing certain wavelength bands (spectral bands) included by the light emitted, transmitted or reflected by the object, or a more continuous wavelength distribution of the light (continuous spectrum). It is particularly typical for spectrum separating methods that they utilize the spectral characteristics of the light measured from the object, or, more generally of the electromagnetic radiation, to determine a certain quality variable. In methods based purely on imaging, the detection of light typically occurs without actual spectrum separation by using only one wavelength band, which wavelength band is often determined according to the wavelength sensitivity of the detector.

Because the abovementioned methods, which are based on spectrum separation, can be considered to represent the closest prior art from the point of view of the current invention, they will be discussed in more detail in the following.

U.S. Pat. No. 4,733,078 presents equipment for measuring the moisture level of a paper web, wherein radiation from the infrared range is directed from a light source through the paper web in such a manner that the radiation, which has penetrated the paper web, is measured successively in time on several spectral bands to determine the moisture level of the paper web. An obvious problem of this solution is the difference in time of the measurements taken on different spectral bands, in which case when using data measured on different spectral bands at different times for determining the moisture level of the web, the measurement result obtained in this manner does not describe a certain point of the web exactly, but the measurement result is naturally affected by the movement of the web during the measurement.

U.S. Pat. No. 3,641,349 discloses equipment, in which radiation of the infrared range, which has penetrated a paper web, is divided into several optical branches, each optical branch being directed through a separate wavelength filter to a separate detector. By modulating the radiation directed through the paper web in a suitable manner, it is possible to perform the measurement simultaneously on all the examined spectral bands, i.e. in a temporally parallel manner, in which case the moisture value of the web, obtained as a result of the measurement, better represents a certain local range of the web. One limitation of the method is that the number of spectral bands being examined is, in practice, limited, because the complexity of the measurement equipment increases significantly with an increase in the number of spectral bands. Because of the number of detectors the costs of measurement equipment can also be high.

The applicant's previous patent application WO 99/14579, which has become public, further discloses measurement equipment, wherein infrared radiation is directed from the light source through a moving paper web, and the radiation, which has penetrated the paper web, is further led to a spectrograph for spectrum separation. By means of this arrangement it is possible to measure, instead of a few separate spectral bands, a more continuous spectrum of the radiation with the help of a matrix detector installed on the output level of the spectrograph. Thus, in the measurement, all the examined so-called wavelength channels are measured at the same time, i.e. temporally in parallel with each other. Thus, as the measurement result the momentary continuous spectrum of the measuring point can be determined in a certain wavelength range, in which case the accuracy of determining the characteristics of an object, such as the moisture level of the web or other examined quality variable, on the basis of the aforementioned spectral data, is better than when determining the quality variable on the basis of only a few spectral bands, which are measured, for example, by using separate and parallel optical filters.

U.S. Pat. No. 5,019,710 discloses equipment, by means of which the measurement based on spectral separation can be performed across the entire cross-directional width of the fiber web without needing to traverse the optical measurement device, i.e. to move it mechanically in cross-direction of the web. The solution presented in the U.S. Pat. No. 5,019,710 is based on the use of optical fibres in such a manner that the measuring point is traversed for different points in the cross-direction of the web by multiplexing the optical device, which performs the actual measurement and comprises a light source and a detector part, to optical fibre pairs arranged at different points of the web, in which optical fibre pairs one of the optical fibres placed on different sides of the web conducts light from the light source to the web, and correspondingly the other conducts the light from the web to the detector part.

Furthermore, publication WO 99/02941 presents the measuring of the thickness of a paper web in such a manner that a measuring beam is led to the paper web with optical fibres, and the radiation, which has penetrated the web, is further conducted to an optical measurement device. In this solution, the optical fibres are arranged side by side in the cross-direction of the web substantially across the whole width in the transverse direction of the web. According to one embodiment presented in the publication, measurement of the continuous spectrum in the cross-direction of the web in all measuring points is performed simultaneously by means of parallel miniature spectrometers.

In a summary, it can be stated that by using the arrangements of prior art in order to determine the characteristics of the web, it is possible to implement different kinds of spectrum separated optical measurements in such a manner that the measurements cover substantially the entire cross-directional width of the web and either individual spectral bands or a continuous wider spectral range is measured at each measuring point. Temporally, the measurement can be implemented in such a manner that the measurement of the cross-directional profile of spectral data is implemented in the transverse direction of the web at all measuring points substantially at the same time (without traversing), and at each measuring point all the wavelengths being monitored are registered substantially at the same time (in a temporally parallel manner).

In the above-described spectrum separated measurements according to prior art, the time elapsed in the measuring, during which time the web being examined thus continuously travels past the monitoring point, is, according to the opinion of the applicant, discussed only in the following senses in the development of measurement methods. Firstly, there is an aim to develop the measurement methods in such a manner that the measurement information is registered simultaneously across the entire width in the transverse direction of the web without mechanical traversing or the like. The aim is thus for the measurement to efficiently cover the entire area of the web. Secondly, there is an aim to develop the measurement methods in such a manner that the individual spectral bands or the continuous spectrum being examined in each cross-direction measuring point of the web are to be measured temporally at the same time, in which case an interesting characteristic of the web that is to be determined by using them, such as moisture, represents the point of the web more accurately without the movement of the web affecting the measurement result.

Basic Principle and Most Important Advantages of the Invention

The primary aim of the present invention is to provide a novel method for controlling quality and condition on the basis of spectrum separating measurement, to be used in processes for manufacturing and/or finishing a continuous fibre web.

The aim of the invention is to utilize, significantly more efficiently than in prior art, the possibility to perform optical spectrum separated measurements on the web or its path, with a good temporal and spatial resolution. The aim of the invention is thus further to make it possible to collect significantly more diverse and detailed data from an object being measured than with prior art methods, and further to automatically analyse the measurement results significantly more efficiently with a computer or the like.

It is a particular aim of the invention to make it possible to observe more accurately than in prior art, and reliably identify fast phenomena, which appear only momentarily in the so called machine direction in the process. The invention is also applicable, however, for analysing more continuous phenomena. A very significant advantage of the invention is that the cause of failures in the process can now be identified by means of the invention in an easier and more reliable way than in prior art. Thus, the invention makes it possible to implement a highly automated control of quality and condition.

The essential basic idea of the invention is that temporally and spatially resolved spectral data is collected with the optical spectrum separating measurement device from a moving object, i.e. a web or an element involved in handling it, in a manner synchronized with the movement of the object. On the basis of this spectral data, a two-dimensional "quality variable chart" is formed, which chart is further substantially continuous in the direction of movement and describes at least one quality variable.

In this context, the two-dimensional quality variable chart refers to a method of storing data, in which the data is stored in a coordinate system, its first axis describing a point in the cross-direction of the object (such as, for example, the web), and the second axis of the coordinate system describing a point in the direction of movement of the object. At each point, which is determined with the help of the two coordinates data on the value of the quality variable is stored.

The quality variable can be, for example, the moisture level of the web or the amount of coating of the web, which quality variables are determined from the web on the basis of, for example, transmission and spectrum separated reflection measurements, which are carried out on the infrared range. Thus the quality variable chart reveals, for example, changes in the moisture level of the web at different points of the web in machine direction and cross-direction.

The quality variable being examined can also be another characteristic of the web, the coating of the web or an element connected to the handling of the web, which is determined, for example, by means of spectrum separated measurements performed on the visible range. The quality variable can thus be, for example, the colour, opacity, brightness, gloss, or smoothness of the object.

According to the invention, to determine the characteristics of the object and/or in order to detect defects in the object, local deviations and/or discontinuities, especially in the direction of motion of the object, of at least one quality variable are further recognized in the continuous quality variable chart, and the cause of such deviances and/or discontinuities is recognized on the basis of the periodicity of the phenomena in the direction of the movement.

Thus, synchronizing the two-dimensional quality variable chart with the movement of the object will make it possible to detect, in the quality variable chart, recurrent and transient phenomena in the machine direction, in an efficient and, if necessary, automatic way, and furthermore, the causes of these recurrent phenomena can be identified on the basis of the periodicity of the phenomena.

If the object to be measured is, for example, a moving fibre web, the cause of a defect recurring at regular intervals in the web can be identified to be a roll rotating at a known peripheral speed in relation to the web, wherein a damaged or soiled point on the surface of the roll causes a defect in the passing web, recurring at intervals corresponding to the peripheral length of the roll.

In an advantageous embodiment of the invention, the quality variable chart formed of the object or the spectral data used in forming it is averaged in the machine direction across a cycle length specific to the object to be monitored, in order to detect periodical phenomena of lower intensity. The cycle length to be used in the averaging can be selected to correspond, for example, to the peripheral length of a specific roll. Averaging efficiently removes random noise present in the measurement result.

By using the method according to the invention, it is possible to search, in the quality variable chart, for periodical phenomena caused by the object to be measured, or by a component preceding it in the process. Thanks to the collecting of spectral data at good sensitivity, and averaging of the results, it is also possible to detect periodical phenomena in the fibre web, which are caused by (preceding) components located farther away from the point of measurement. As a result, it is possible to monitor more steps (a longer web length) in the process by using only a single measuring point.

The method according to the invention can be applied for monitoring the moving web itself, or for monitoring the condition of rotating/moving means which are involved in the processing of the web and are in contact with it, such as rolls and various textures (wires, felts). The invention is also applicable for monitoring the properties of reels to be formed of the web.

A malfunction of the means involved in the processing of the fibre web can be detected either by direct measurement of the means or on the basis of a marking caused in the passing web by the means.

The measurement according to the invention can be carried out in relation to the direction of movement of the object being examined across the entire width in the transverse direction of the object or only partly across the width. When measuring across the entire width of the object, for example a fibre web, the measurement is carried out advantageously by using such a measurement arrangement, where the measurement of the cross-direction profile of the spectral data is carried out substantially at the same time across the entire width of the web. Thus the phenomena occurring in the cross-direction in relation to the direction of movement of the object and in the machine direction according to the movement can be reliably distinguished from each other.

The following more detailed description of the invention with examples will more clearly illustrate, for anyone skilled in the art, preferred embodiments of the invention as well as advantages to be achieved with the invention in relation to background art.

BRIEF DESCRIPTION OF THE DRAWINGS

In the following, the invention will be described in more detail with reference to the appended drawings, in which.

DETAILED DESCRIPTION OF THE INVENTION

Figure 1:
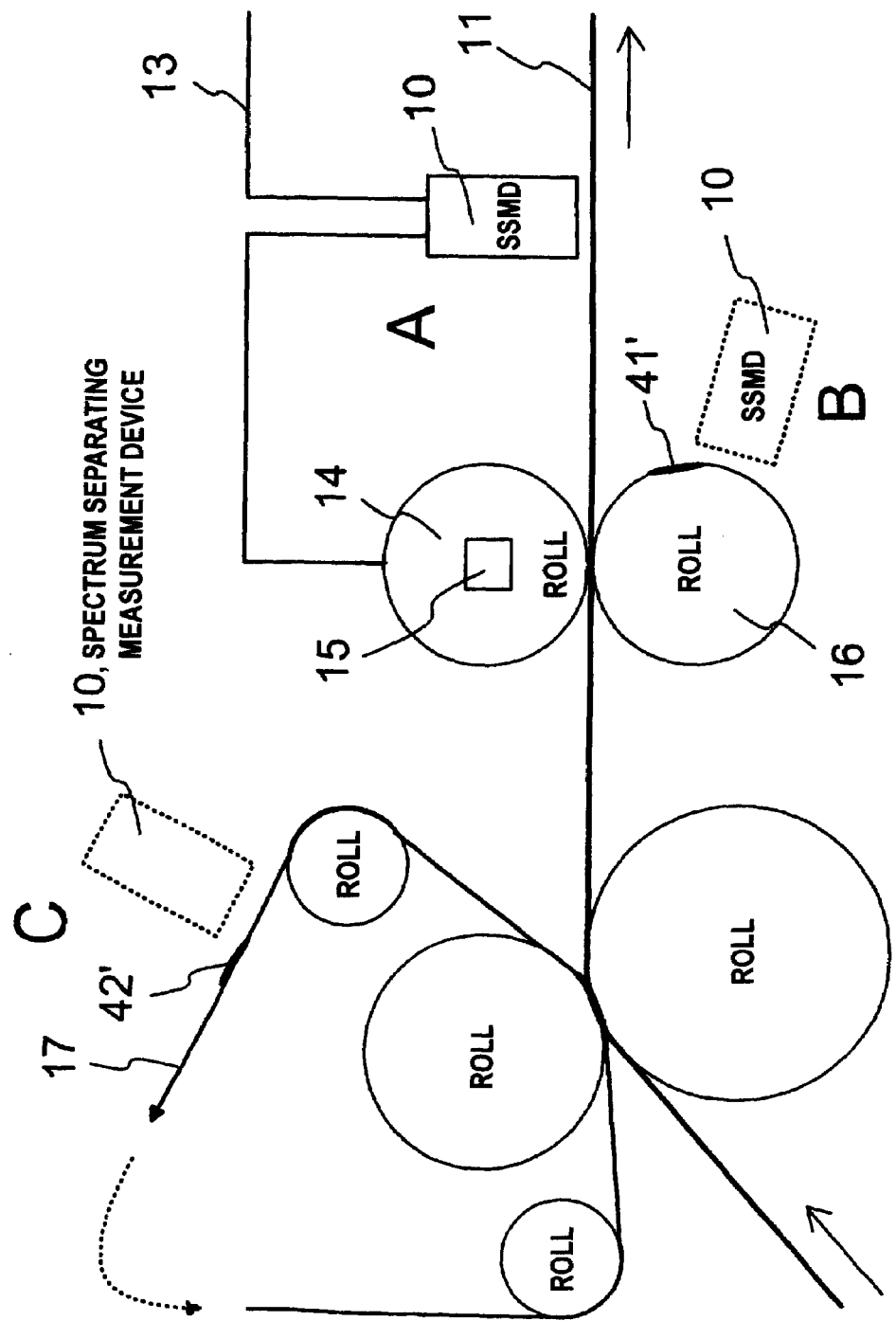
FIG. 1 shows an embodiment of the invention in principle with a measurement device in various positions within the embodiment.

FIG. 1 shows, in principle, some possible embodiments, which correspond to the different placements A, B, C of the spectrum separating measurement device marked in FIG. 1. The invention will be discussed in the following by using the placement A marked in FIG. 1 as an example and the moisture level of web 11 as the quality variable being examined.

A spectrum separating measurement device (SSMD) 10 placed in position A is arranged to collect spectral data from the moving web 11 being measured in order to form a continuous quality variable chart of the web 11 according to the invention. The web 11 can be a fibre web, which can appear in different forms in paper or board manufacturing, and which can, depending on the measuring point be supported from the measuring point also in relation to the measurement device 10 from the opposite side by means of a wire, a roll or another element.

Figure 2:
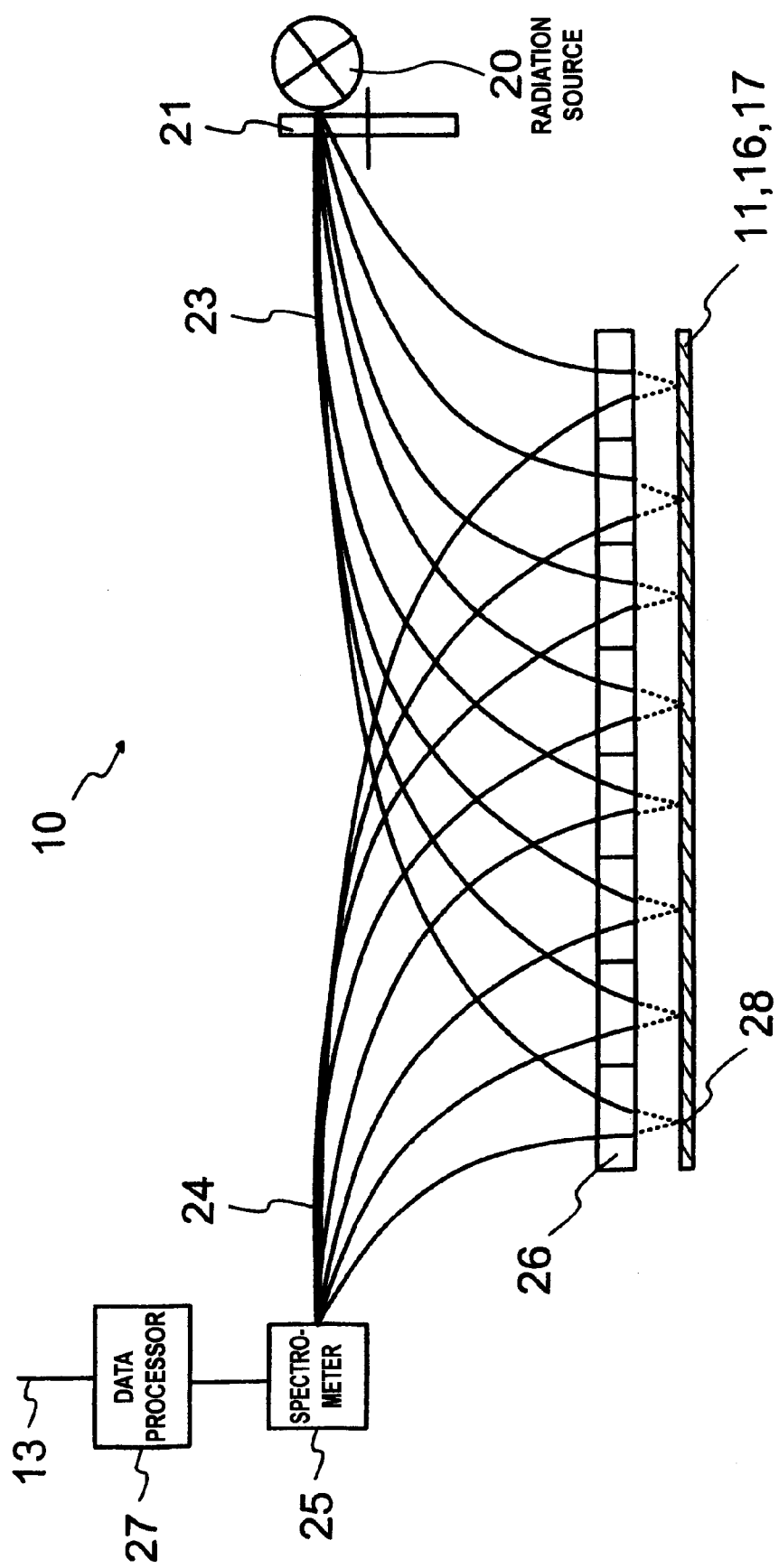
FIG. 2 shows a spectrum separating measurement device applied in the method according to the invention in principle.

FIG. 2 shows a possible embodiment of a spectrum separating measurement device 10 in principle. The measurement device 10 comprises a radiation source 20, which emits radiation preferably in the infrared range when the quality variable is the moisture level of the web. The wavelength of the radiation can be, for example, between 1 to 2.5 µm, but if necessary, the wavelength can be shorter or longer than this, depending on the quality variable being examined. The radiation source can be, for example, a radiator of a black body, a halogen lamp, or another radiation source suitable for the purpose.

When the measurement is taken in the infrared range, there is, if necessary, a chopper 21 arranged after the radiation source 20 to break or modulate the radiation in time in a way known as such. Radiation from the radiation source 20 is led to an object 11, 16, 17 by means of first optical fibres 23. The object can be, as shown in FIG. 1, the paper web 11 as such or another element related to its processing, such as a roll 16 or a wire cloth 17. Radiation reflected from the object 11, 16, 17 is further led with second optical fibres 24 to a spectrometer 25.

The ends of both the first optical fibres 23 and the second optical fibres 24 are arranged at measurement ends 26. In addition, there can be other necessary measurement optics, such as lens or mirror arrangements for controlling the radiation between the ends of the optical fibres 23, 24 and the object 11, 16, 17, arranged at the measurement ends. The measurement ends 26 determine the parallel measuring points 28 in the cross-direction of the object, which are being used in the measurement.

Figure 3:
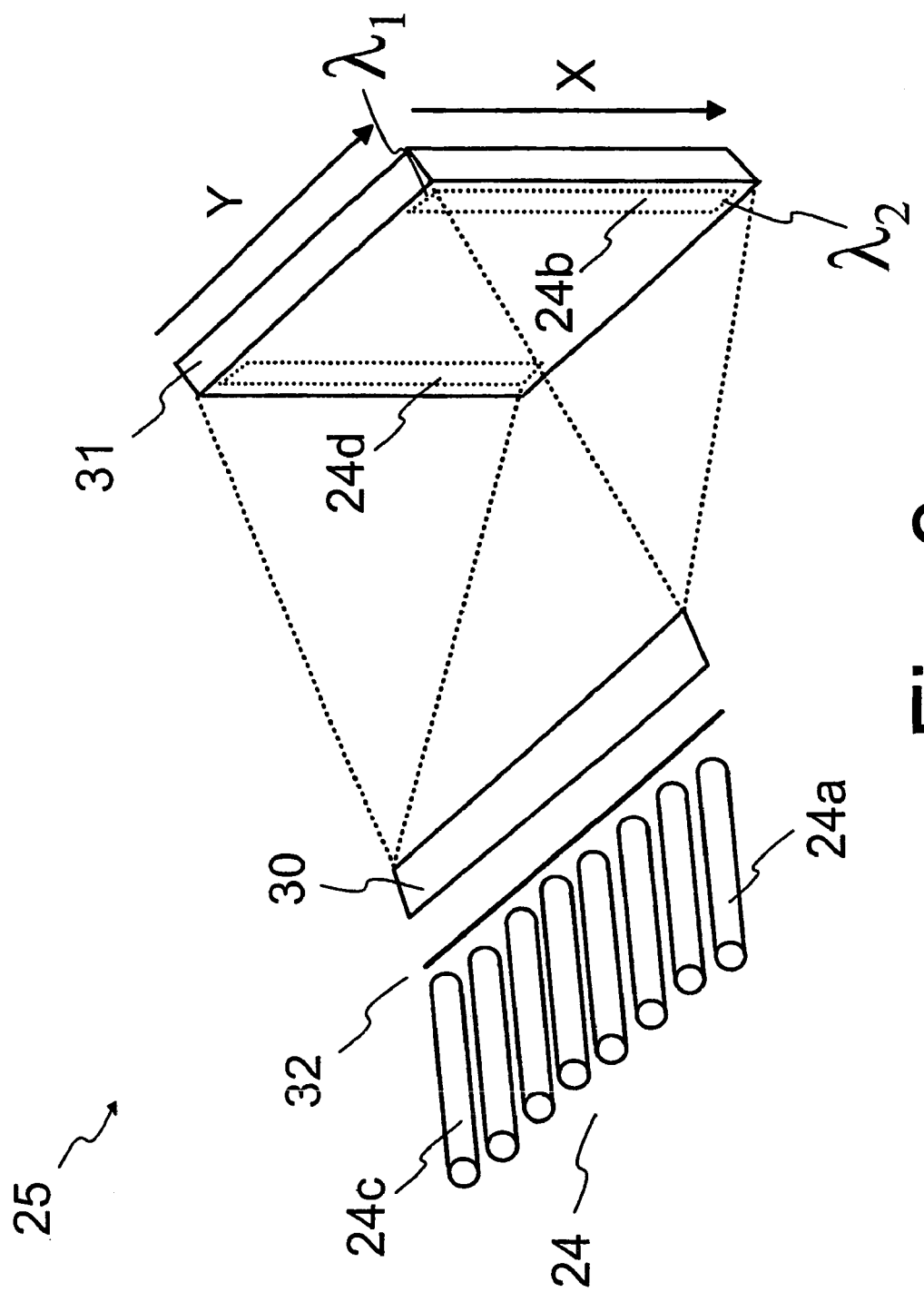
FIG. 3 shows the operating principle of a spectrometer applicable in the measurement device according to FIG. 2 in principle.

The spectrometer 25 comprises according to FIG. 3, at least a spectrograph 30 and a matrix detector 31. The spectrograph 30 is arranged to record light radiation directed from other optical fibres 24 to its entrance port 32 in a matrix detector 31 in such a spectrally separated manner that in the direction Y marked on FIG. 3 a point axis is formed on the matrix detector 31 and correspondingly in direction X a wavelength axis. Thus, for example, radiation from fibre

24a, which belongs to the second optical fibres, is imaged as spectrum 24b on the matrix detector 31, in which spectrum the different wavelengths from the longest wavelength $\lambda_1$ to the shortest wavelength $\lambda_2$ are divided into different points of the matrix detector 31 in the direction of the wavelength axis X. Correspondingly, for example, the radiation from a second optical fibre 24c is imaged as spectrum 24d on the matrix detector. The spectrograph 30 can be, for example, a PGP-type spectrograph (Prism-Grating-Prism), a grating spectrograph, or another prior art device suitable for the use.

Thus, the spectrum separating measurement device 10 makes it possible to measure spectral data on the object 11, 16, 17 in relation to the direction of movement of the object in the cross-direction at several parallel measuring points simultaneously in time. Thus, the momentary cross-directional profile of the spectral data of the object is determined with the measurement device. When the quality variable determined according to the spectral data is, for example, the moisture level, the spectral data is measured preferably in the near infrared range, for example in the wavelength range from 1.0 to 1.7 μm or from 1.0 to 2.4 μm.

The continuous two-dimensional quality variable chart according to the invention is thus formed by means of cross-direction profiles of the spectral data, which are determined from the object at successive moments of time. An individual cross-directional profile of spectral data comprises parallel measuring points in cross-direction, wherein at each parallel measuring point, a continuous spectrum of the object on a certain range is stored substantially at the same time by means of, for example, a spectrograph, or several separate spectral bands are stored by using, for example, parallel optical filters.

When the quality variable being measured is, for example, the moisture level of the web 11, the continuous two-dimensional quality variable chart according to the invention thus describes the changes in the moisture level of the web 11 in a spatially resolved manner both in the cross-direction and the machine direction of the web 11.

In order to implement the quality and condition monitoring according to the invention, the spectrometer 25, which automatically collects spectral data, is arranged according to what is presented in FIG. 2 in a data transmission connection with a data processor 27. In the data processor 27, spectral data is first converted to a continuous two-dimensional quality variable chart, which quality variable chart is further analysed to determine the properties of the object 11, 16, 17 and/or to detect defects in the object, and to recognize the causes of the phenomena. The data processor 27 can be, for example, a microcomputer or the like, which is equipped with software suitable for the purpose.

The data processor 27 of the spectrum separating measurement device 10 can further be arranged in a data transmission connection 13 with the other equipment controlling the processing of the web 11. This makes it possible, for example, to make adjustments automatically on the basis of measurement results determined from the quality variable chart. By means of the data transmission connection 13, it is also possible to implement alarming of the user or other measures when certain predetermined limit values are exceeded.

Preferably, the data processor 27 is equipped with a user interface, such as a display and a keyboard, for displaying data to the user and for receiving settings and function commands from the user.

In order to synchronize the quality variable chart according to the invention with the movement of the object 11, 16, 17 being measured, the spectrum separating measurement device 10 is connected with a means measuring the speed of motion of the object. According to FIG. 1 the means can be, for example, in contact with the web 11, being a pulse sensor 15, which is installed in the core of a roll 14 rotating at a peripheral speed corresponding to the rate of propagation of the web. The pulse sensor 15 is arranged to produce one or more pulses for each one rotation of the roll 14. When the peripheral length of the roll is known, it is possible to determine the exact rate of propagation of the web 11 on the basis of the pulses obtained from the pulse sensor 15.

Alternatively, the spectrum separating measurement device 10 and the data processor 27, incorporated in it, may obtain the data about the speed of motion required for the synchronization via the data transmission connection 13 from the equipment controlling the processing of the web 11, such as, for example, the control system of a paper machine.

The spectrum separating measurement device 10 can be arranged to measure the web 11 (or another object) across the entire so-called production width of the web in the cross-machine direction, or the measurement can also be focused on a narrower range than the production width.

In position B in FIG. 1, the spectrum separating measurement device 10 is arranged to measure the surface of a roll 16 in synchronization with the rotational speed of the roll 16 in such a way that a continuous quality variable chart about the surface of the roll 16 is recorded in the data processor 27. As a result of the synchronization, it is possible to separate from the continuous quality variable chart a section corresponding to each one rotation of the roll 16 to a so-called matched two-dimensional quality variable chart. In such successive and matched quality variable charts, the same specific point in the two-dimensional chart will thus always correspond to one and the same specific point on the surface of the roll 16. The matched quality variable charts can further be analysed with the data processor 27, for example, by averaging the quality variable charts in such a manner that in successive and matched charts the quality variables corresponding to the same point in the object, i.e. for example moisture values, are averaged with each other.

In position C of FIG. 1, the spectrum separating measurement device 10 is arranged to measure a moving texture 17 interacting with the web 11 in a way synchronized with the speed of rotation of the texture 17. The texture 17 can be, for example, a so-called drying felt or wire. According to the invention, a continuous quality variable chart, for example a moisture chart, is now formed in the data processor 27 in the same way as above. From this continuous quality variable chart, it is further possible to distinguish single matched quality variable charts corresponding to one rotation of the web 17, for a more detailed analysis and/or for averaging.

From a two-dimensional quality variable chart determined with a good temporal and spatial resolution, it is now possible, according to the invention, to detect phenomena occurring only momentarily or also more continuously in the machine direction. In the following, the analysis of quality variable charts formed according to the invention will be described in more detail, now with reference to FIGS. 4 to 6.

Figure 4:
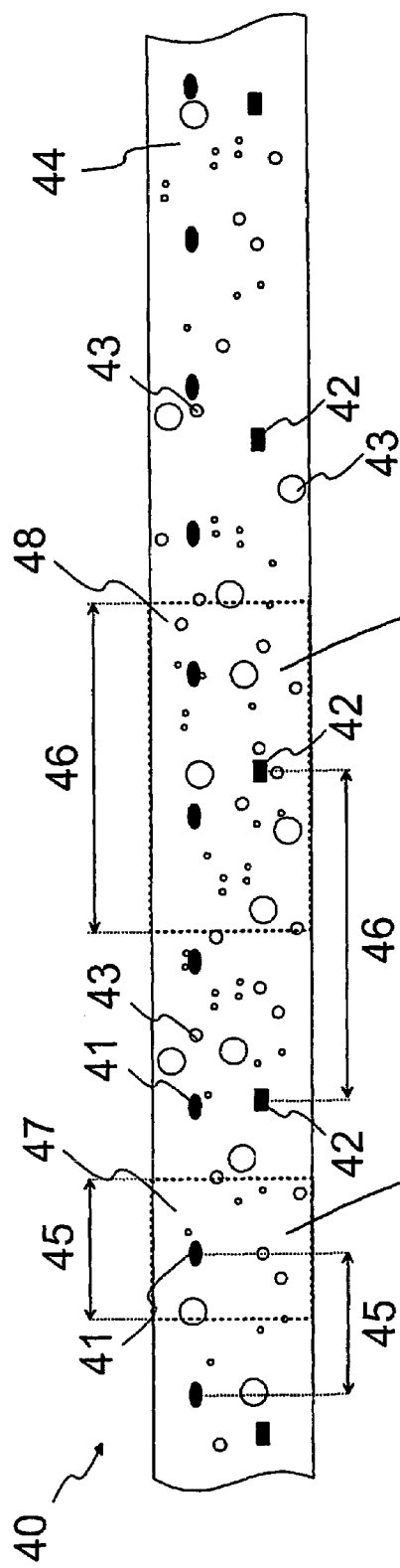
FIG. 4 illustrates a continuous two-dimensional quality variable chart formed according to the invention in principle.

FIG. 4 presents, in principle, a continuous 2-dimensional quality variable chart 40 according to the invention. The chart mentioned in this example can be considered to be formed with the spectrum separating measurement device 10 placed in position A in FIG. 1 and by synchronizing the imaging with the movement of the web 11. In the following, the moisture level of the web will be used as an example of the quality variable being monitored, in which case the wavelengths measured by the measurement device 10 are selected appropriately for this purpose from the near infrared range.

In the following examples, the quality variable chart 40 thus describes the local distribution of the moisture level of the Web 11 across a given length of the web 11. In the quality variable chart 40 of FIG. 4, the horizontal direction (the first dimension) thus corresponds to the different regions of the web in the machine direction, and the vertical direction (the second dimension) corresponds to the different regions of the web in the cross-direction.

In the continuous quality variable chart 40, the areas marked with black ovals 41 and black rectangles 42 as well as light circles 43 of different sizes indicate points at which the moisture detected by the spectrum separating measurement device 10 differs within the measuring accuracy from the moisture of the background 44 of the quality variable chart 40 illustrated as white. It is obvious that in reality, the background 44 of the quality variable chart 40 consists of a large number of points and areas differing from each other to some extent in their moisture level. Similarly, for example recurrent areas 41 marked with black ovals do not recur in exactly the same size and moisture level at different parts of the quality variable chart 40. Primarily for reasons of the drawing technique and clarity, the background 44 and the areas 41, 42, 43 in FIG. 4 are illustrated with simplified shapes and moisture levels.

In this example, the areas 41 recurring in the continuous quality variable chart 40 of FIG. 4 are caused by local damaging/soiling 41' of the coating of the roll 16 shown in FIG. 1. In a corresponding manner, the areas 42 are caused by local damaging/soiling 42' of the texture 17 shown in FIG. 1. The areas 44 indicate minor random moisture changes occurring in the web 11 for various reasons.

According to the invention, the continuous quality variable chart 40 can now be analysed by dividing it into matched quality variable charts and further by averaging the matched quality variable charts with each other. The cycle length of the matched quality variable charts, which corresponds to the direction of propagation of the web 11, is selected on the basis of the part or means with which the web 11 is in contact in its path and about which more data is needed.

Figure 5:
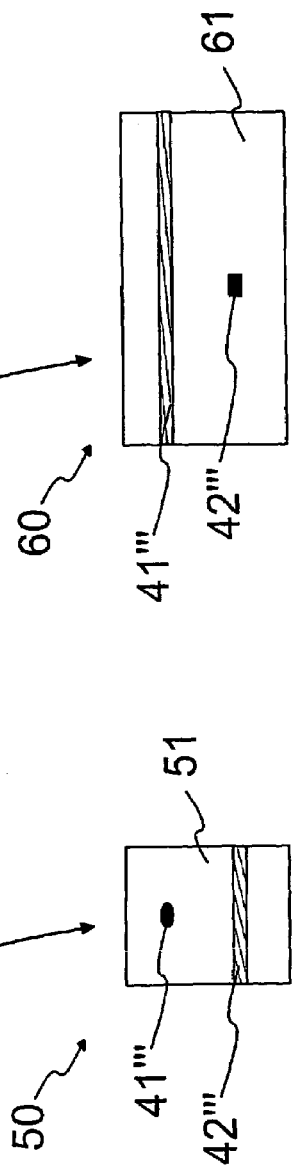
FIG. 5 shows, in principle, a matched quality variable chart obtained from the continuous quality variable chart of FIG. 4 by averaging across a given interval.

FIG. 5 shows an averaged matched quality variable chart 50, which is formed by dividing the continuous quality variable chart 40 into partial charts 47 having the length of a cycle 45. In this case, the length of the cycle 45 now corresponds to the peripheral length of the roll 16.

To form the averaged and matched quality variable chart 50, the partial charts 47 are averaged together in such a way that the points corresponding to the same pixel in successive partial charts 47 are averaged together. In other words, in this example, the same pixel in the successive partial charts 47 always corresponds to the same point on the surface of the roll 16. In the matched quality variable chart 50 obtained as a result of the averaging, the moisture deviation caused by damaging/soiling 41' of the roll 16 is detected as a distinctive area 41''' whose moisture differs from the moisture of its surroundings. However, local damaging/soiling 42' of the texture 17 is detected as a weaker, streak-like phenomenon 42''' occurring across the whole averaged quality variable chart 50. The reason for this is that when the peripheral length 45 of the roll 16 is used as the cycle length in the averaging, the cycle of occurrence of the damaging/soiling 42' of the texture 17 does not correlate with the cycle length 45.

Figure 6:
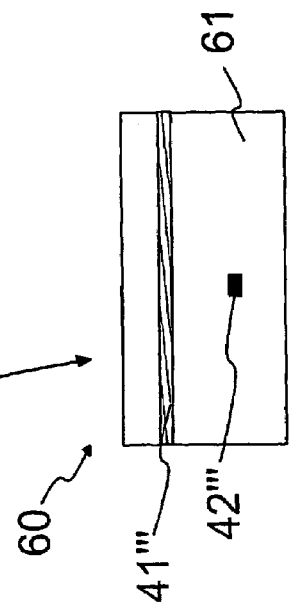
FIG. 6 shows, in principle, a matched quality variable chart obtained from the continuous quality variable chart of FIG. 4 by averaging across another interval.

FIG. 6 shows an averaged and matched quality variable chart 60 formed in a corresponding manner by dividing the continuous quality variable chart 40 into partial charts 48 according to a cycle length 46. Now, when the cycle length 46 correlates with the cycle of occurrence of damaging/soiling 42' of the texture 17, the corresponding moisture deviation 4''' is clearly visible in the averaged quality variable chart 40. In this situation, the change in the moisture level caused in the averaged and matched quality variable chart 40 by areas 41 occurring at cycle lengths 45 in the continuous quality variable chart 60 is, in turn, distributed in a corresponding manner across the area corresponding to the entire length of the quality variable chart 60.

Moisture deviations 44, which occur at random in the continuous quality variable chart 40 and do not correlate with the cycle lengths 45, 46 used in the formation of matched quality variable charts 50 and 60, are levelled out in the averaged quality variable charts 50 and 60 as backgrounds 51 and 61. Using a sufficiently long averaging, it is thus possible, in the method according to the invention, to efficiently reduce random noise occurring in quality variable charts. Such random noise occurs, for example, in a situation, in which the measurement is disturbed by water mist or water spraying occurring between the spectrum separating measurement device 10 and the object 11, 16, 17 to be measured. Such a situation is typical when the measurement is performed, for example, in the wet end of a paper machine. Random noise can also be caused by the spectrum separating measurement device 10 itself, wherein the amount of light available for use in measuring spectral data is small.

The averaging, which improves the accuracy of measurement results, can also be performed in such a manner that the spectral data, which is collected in a synchronized manner in relation to the movement of the object being measured, is averaged in a matched manner even before the quality variable being observed is determined of the spectral data in question. This type of averaging of a "raw" signal improves the measuring accuracy especially in such a situation, where the signal/noise ratio of the spectral data received as a result of an optical spectrum separated measurement is weak. Such a situation may arise, for example, when spectral data is to be measured with a great spatial, temporal and wavelength resolution, in which case the amount of light coming to the detector/detectors is small.

Figure 7:
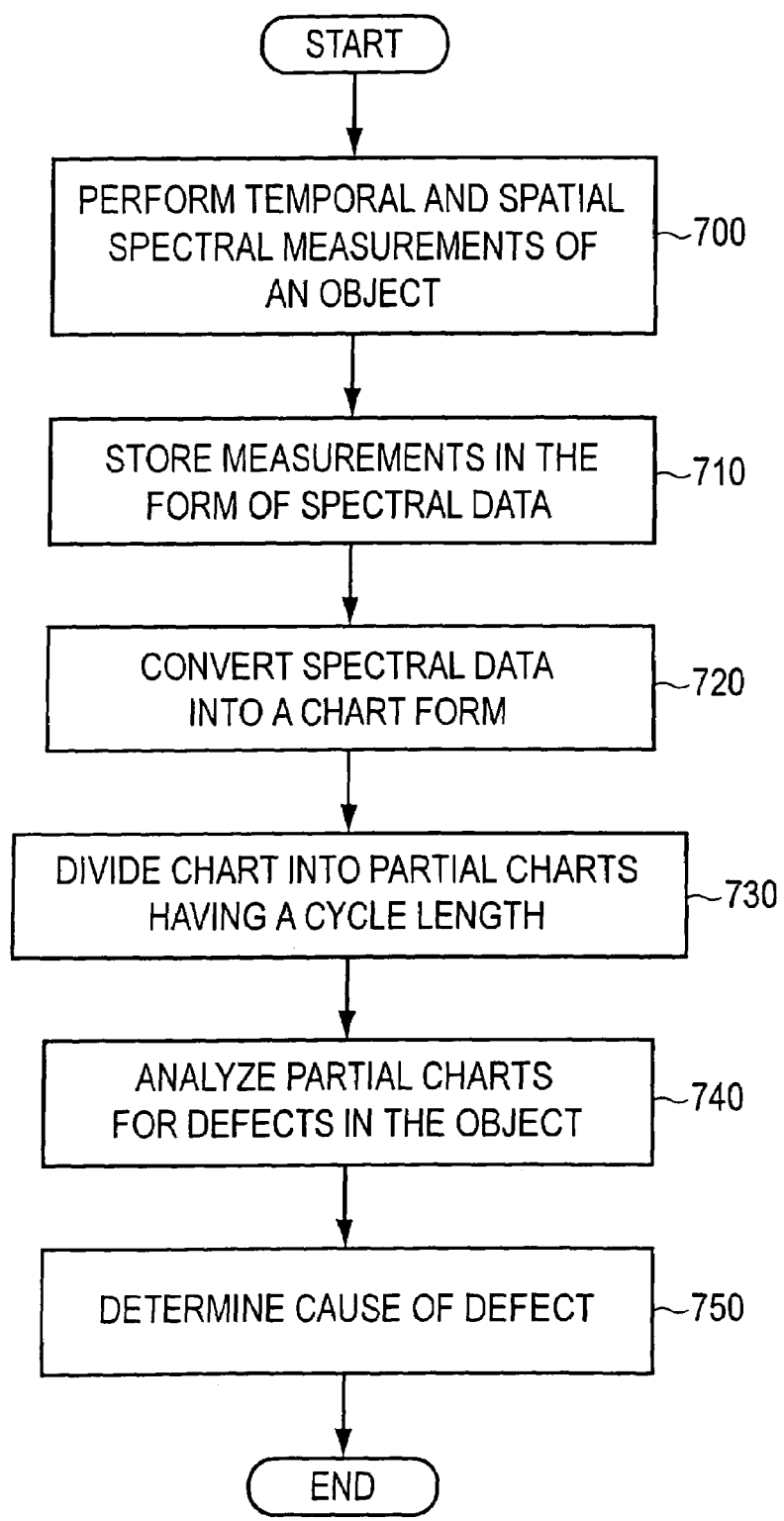
FIG. 7 shows a flow chart of a method for controlling the quality of a fibre web in a manufacturing process.

FIG. 7 shows a flow chart of a method for controlling the quality of a fibre web in the process for manufacturing the fibre web. The method begins with a monitoring step 700 by performing temporal and spatial measurements of an object, such as a fibre web. The measurements can be spectral measurements of electromagnetic radiation transmitted, reflected, or emitted from the object, and can be performed by an optical spectrum separating measurement device 10. At step 710, the measurements are stored in the form of spectral data. During step 720 the spectral data is converted into a chart, such as a continuous two-dimensional quality variable chart according to the invention. This conversion can be performed by a data processor 27. Further, at step 730, the chart is divided into partial charts having a cycle length. The cycle length can correspond to a length of influence of a rotating or moving means in the process for manufacturing the object. At step 740, the partial charts are analysed for defects in the object. The defects can be represented by deviations or discontinuities of a quality variable in the partial charts. Finally, at step 750, the cause or causes of the defects are determined. Because the measurements of step 700 and the analysis of the measurements of step 740 can be synchronized with the movement of the object, the cause of the defect can be allocated to a specific location on the rotating or moving means.

Consequently, the method according to the invention makes it possible to detect the cause of the phenomena detectable at a measuring object, such as web 11, on the basis of the recurrence of the phenomena. The phenomena may be caused by means located immediately before the measuring point, or also by means located farther away from the measuring point. Typically, a "mark" caused in the web 11 by a means located farther away from the measuring point is, to some extent, faded when arriving at the measuring point; therefore, its detection will typically require the longer averaging, the farther away from the measuring point the means causing the mark is located.

Although the invention has been described above primarily for the purpose of detecting transient spot-like defects in the direction of movement of the object to be measured, it is obvious that the invention can also be used to detect various defects of longer duration or extending longer in the direction of movement, i.e. streak-like defects. In a streak-like defect, which is continuous in the direction of movement, the recurrence of the defect in the direction of movement and thereby the cause of the defect can be identified, for example, as recurrent variation in the width of the streak and/or as recurrent "twisting" of the streak in the direction transverse to the direction of movement. In discontinuous streaks, i.e. streaks occurring as stretches, the recurrence can be identified, for example, on the basis of the moments of starting and/or ending of the streak.

Further, the defects detectable by means of the method can be, in the same way as spots, narrow in the cross-direction, or the defects can also extend to a wider range in the cross-direction, all the way to the production width. Wider defects in the cross-direction, which are detectable by the method may include, for example, whipping of the web, which will be discussed in more detail in connection with the embodiments of the invention herein below.

Thus, the only precondition, which is substantial in view of the invention, is that some kind of recurrence in the direction of movement can be identified in the defect to be detected on the basis of a local deviation in the quality variable being examined, by means of which recurrence the cause of the defect can be further determined.

Preferably, the measurement according to the invention is performed in such a way that a portion of the continuous quality variable chart 40 with a certain length is recorded in the memory of the data processor 27 of the spectrum separating measurement device 10. After this, the continuous quality variable chart 40 stored in the memory is analysed by dividing it into matched partial charts 47, 48 having the length of a given cycle. The matched partial charts 47, 48 can further be averaged to form averaged and matched quality variable charts 50, 60. As mentioned before, averaging can also be performed on spectral data, in which case the quality variable for a matched quality variable chart is determined only after averaging of a "raw" signal. The cycle length 45, 46 to be used in the formation of matched quality variable charts can be selected of predetermined cycle lengths which have been stored in the memory of the data processor 27 and which correspond to the peripheral lengths of different rotating/moving rolls or textures, or the like, in the apparatus to be monitored. The continuous quality variable chart 40 is analysed by using the known different cycle lengths one after the other.

Alternatively, it is also possible that the data processor 27 automatically scans different cycle lengths at a range determined by the user, looking for any cycle length at which an obvious correlation is detected in the averaged and matched quality variable chart 50, 60. When such a correlation is detected, an attempt is made to identify its cause on the basis of the corresponding cycle length from the data about the process apparatus stored in the memory of the data processor 27 in advance. If necessary, the user is also informed of the correlation.

Naturally, it will be obvious for anyone skilled in the art that the data processor 27 can be implemented in such a way that a continuous quality variable chart 40 stored in the memory of the data processor 27 is efficiently processed by using, for example, several cycle lengths 45, 46 simultaneously in parallel in the computation. This can be implemented, for example, by two or more processors operating in parallel and analysing, by different methods, the same continuous quality variable chart 40 stored in the memory. Further, the data processor 27 can also be implemented in such a way that when analysing the continuous quality variable chart 40 stored in the memory, the signal generated by the spectrometer 25 is simultaneously stored in another location in the memory of the data processor 27, in which case no measuring information produced by the spectrometer 25 is lost during the analysis. The embodiments make it possible to produce measuring information about the object to be measured substantially in real time, which will further make it possible to quickly intervene in the process to be monitored, automatically or manually by the user.

EMBODIMENTS OF THE INVENTION

In the following, some embodiments will be presented to exemplify the application of the method according to the invention in processes for manufacturing and/or finishing paper, board, or a corresponding material.

A local blockage or damage in a texture used for drying a fibre web, such as a drying felt, can be detected by direct measurement, according to the invention, of the surface of the drying felt. Thus, a local deviation in, for example, the moisture level will be detected in the matched quality variable chart of the felt recorded during its single rotation, or in a matched and averaged quality variable chart computed on the basis of several rotations. The same malfunction of the drying web can also be detected on the basis of the recurrent "marking" of the drying web in the passing fibre web, by measuring the fibre web to be processed. At that point of the fibre web, which corresponds to the blocked point in the felt, or the like, the moisture of the web differs from the moisture in the surrounding area of the web, which is detected as a deviation in the quality variable chart. The farther away from the component causing the defect the measurement of the web is taken, the longer the averaging which is typically required to detect the phenomenon, because it fades as the distance becomes longer.

By measuring the drying felt or another texture interacting with the web, or the marking caused by the texture in the web, it is also possible to detect, for example, malfunctions of washing sprays cleaning the texture, and/or defects in the cross-direction profile of the press section pressing the texture and the web against each other. Typically, a defect in the cross-direction profile of the nip between two opposite rolls in the press section may be caused, for example, by curving of the rolls in the direction of the longitudinal axis (incorrect crowning) or by dirt or other material adhered locally to the surface of the rolls.

Among other things, it has been found in tests performed on a test paper machine that with the method according to the invention it is possible to detect the effect of high pressure water jets used in washing the felts of a paper machine on the moisture profile of the paper web, which interacts with the felts.

The effect of nip vibrations, i.e. unfavourable temporal changes in the nip force, can be detected in the quality variable chart as so-called whipping of the texture or the web to be processed, which passes through the nip. Whipping refers to the formation of stripes in the cross-direction in the object being examined, caused by temporal variations in the nip force and thereby further, for example, variations in the drying capacity. The cycle length of nip vibrations is typically significantly shorter than the peripheral length of the rolls forming the nip.

The textures used in manufacturing and/or finishing processes of paper and/or board, in connection with which the method of the invention can be applied, include not only the above-mentioned drying felt but also various wires and belt rolls. By means of the invention, it is also possible to detect obstructions in the suction roll on the basis of a marking caused by the suction roll in the fibre web, by synchronizing the measurement of the fibre web with the rotation of the suction roll.

The method of the invention is also suitable for controlling the condition of so-called soft rolls, which are coated. Soft rolls are used, for example, in the calendering of paper, wherein the paper web is guided through one or more so-called calender nips. The calender nip is formed between a hard-faced metal roll and a soft-faced coated roll. The nip can also be formed between two soft-faced rolls. In soft-faced rolls used in modern calenders, the metal roll frame is typically coated with a polymer material. The polymer coating of the roll may be damaged during the use, for example, when extra solid material is passed through the nip, causing a momentary and local increase in the nip force, a kind of a pressure impact, which damages the roll coating locally. The coating damage can also be caused by the temperature of the coating, which increases, for some reason, locally to a level, which is too high for the polymer material used. Factors affecting the temperature of the coated roll include, for example, a change in the heat transfer properties caused by a dirt layer adhered to the roll, or other changes in the nip contact, particularly when heated backing rolls are used.

Using the method according to the invention, the condition of the soft-faced roll can be monitored by measuring the surface of the roll in synchronization with the rotation speed of the roll and thereby forming a matched two-dimensional quality variable chart of the surface of the roll in accordance with the invention. If necessary, several matched quality variable charts corresponding to one rotation of the roll can be averaged, as described above. Defects in the roll coating are detected, for example, as reflecting characteristics differing from the surrounding roll coating either as local areas of roll coating, as whipping of the roll coating, or as variations across the whole width of the roll in the machine direction.

Applying the method of the invention, it is also possible to detect, in connection with coated rolls, such transient phenomena, which cannot be properly detected by methods of prior art. Such phenomena include, for example, in the processing of a coated paper web, local variations in the quantity of coating material carried by the paper web onto the roll, that is, so-called wet coating spots, coating streaks or other transient coating defects. When passing through the calender nip and adhering to the coated roll, such coating defects may cause not only a variation in the quality of the final product but also actual damage to the roll coating.

When applying the method of the invention, it is possible to detect such a problematic situation quickly and thereby to reduce the probability of causing a coating defect or to prevent the coating damage from becoming worse. Quick detection of the problematic situation will also reduce the production of a final product of poor quality.

By means of data obtained about the condition of the coated roll substantially in real time, it is also possible to plan the maintenance of the rolls better and to avoid unforeseen and unnecessary stoppages. The condition of the roll coatings can also be controlled by measuring the fibre web to be processed, wherein defects occurring in roll coatings are detected by means of recurrent marking of the fibre web. The control of the fibre web by imaging has the advantage that measurements made at one measuring point can thus be used to control a longer web length. For example, in a calender, the condition of several soft rolls can be monitored by means of one measuring point placed after the calender.

Furthermore, the invention is also suitable for detecting local defects in the coating of a coated web. Thus the measurement can be performed, for example, on a visible wavelength range as a reflection measurement, in which case a local defect in the coating of the web is detected as a deviation in the intrinsic reflectance factor of the web.

By means of the present invention, it is thus possible to control, in a considerably more versatile way than before, various properties of components used in processes for manufacturing or finishing a fibre web, as well as properties of the web to be manufactured or finished.

At a certain measuring point, the measurement width can be selected to be suitable for each case. The measuring can be performed in a direction transverse to the direction of movement of the object, for example for an area with the width of one meter, which area is moved in the cross-direction alternatively at different locations of the production width. Momentarily, the measuring can be extended to take place across the full width of the web, wherein it is also possible to detect wider deviations in the cross-direction. At a certain point of the web, in order to more accurately analyse the phenomenon detected in its cross-direction, the measurement can be focused on the cross-direction area only.

Thanks to the synchronization with the movement of the object to be measured, the method of the invention can also be applied in a situation in which the movement of the object is accelerating or decelerating.

By combining the modes and apparatus structures presented in connection with the different embodiments of the invention presented above, it is possible to provide various embodiments of the invention, which comply with the spirit of the invention. Therefore, the above-presented examples must not be interpreted as restrictive to the invention, but the embodiments of the invention can be freely varied within the scope of the inventive features presented in the claims herein below.

For example, the spectrum separating measurement device used in the method according to the invention can naturally be implemented also in other ways than that presented in FIG. 2. By arranging, for example, an adequate number of measurement devices known from publication WO 99/14579 in parallel in the cross-direction of the object being measured, it is possible to collect spectral data required to form a quality variable chart according to the invention from the object. The measurement can, if necessary, be implemented also without using optical fibres.

In addition, the spectrum separating measurement device (or devices) used in the measurement can further be based on, instead of the use of a spectrograph 30 and a matrix detector 31 or corresponding components, the use of parallel optical filters and separate detectors installed after them, for example, in the manner presented in U.S. Pat. No. 3,641,349.

A measurement applying the method according to the invention is not limited only to measurements taken in the infrared range, but depending on the quality variable being examined, the wavelength range being measured can be freely selected according to the application in question. When the quality variable being examined is the moisture level or the amount of coating of a paper web, the measurements are taken advantageously on the infrared wavelength range. When measuring the characteristics of the coating, the measuring wavelengths can be selected to correspond to the wavelengths characteristic to cellulose, lime or latex. When measuring the colour, brightness, glare or smoothness of the paper web, or the condition of the roll coating, the measurement can be performed, for example, in the visible wavelength range as well. The measurements can be performed, according to the need in each case, for example, on the upper or lower surface of a felt or the web.

According to the invention, spectral data on the object being examined can be collected by measuring electromagnetic radiation, which has transmitted, reflected or otherwise emitted by the object. The light source or sources possibly required in the measurement are thus placed in a manner suitable and appropriate for each method of measurement.

It is obvious that that the two-dimensional quality variable charts presented as functions of locations in FIGS. 4 to 6 can also be presented as so-called three-dimensional quality variable charts, in which case, at each point of the two-dimensional chart, the value of a quality variable is graphically represented on its own third coordinate axis.

The invention claimed is:

1. A method of controlling the quality and/or condition of a fibre web in a process for manufacturing and/or finishing the fibre web, which comprises:
   monitoring the fibre web with at least one optical spectrum separating measurement device;
   determining at least one quality variable of the fibre web;
   performing temporal and spatial measurements of transmitted, reflected, or emitted electromagnetic radiation from the fibre web, synchronously with a movement of the fibre web, using the at least one optical spectrum separating measurement device, and storing the temporal and spatial measurements in the form of spectral data;
   generating a continuous quality variable chart using the spectral data, wherein the continuous quality variable chart is substantially continuous in the direction of movement of the fibre web and represents the at least one quality variable as a function of the position of the at least one quality variable on the fibre web;
   dividing the continuous quality variable chart into successive matched partial charts having a cycle length, wherein the cycle length corresponds to a length of influence of a rotating/moving means in the process for manufacturing and/or finishing the fibre web;
   detecting deviations and/or discontinuities of the at least one quality variable from the successive matched partial charts; and
   detecting malfunctioning of the rotating/moving means using the detected deviations and/or discontinuities of the at least one quality variable.

2. The method according to claim 1, wherein the cycle length corresponds to a length of a periphery of the rotating/moving means in the direction of movement of the fibre web, or an impact length of a vibration of the rotating/moving means in the direction of movement of fibre web.

3. The method according to claim 1, wherein the cycle length corresponds to a length based on the detected deviations and/or discontinuities in the at least one quality variable from the successive matched partial charts.

4. The method according to claim 1, wherein the successive matched partial charts are formed by averaging the spectral data across the cycle length.

5. The method according to claim 1, wherein the successive matched partial charts are combined to form an averaged and matched quality variable chart.

6. The method according to claim 1, wherein the continuous quality variable chart of the fibre web is formed in a cross-direction in relation to the direction of movement of the fibre web on the basis of a plurality of cross-directional profiles of the spectral data measured at successive moments of time, wherein one of the plurality of cross-directional profiles includes a plurality of parallel measuring points in a direction transverse to the movement of the fibre web, wherein a substantially continuous spectrum or wavelength bands separated from a continuous spectrum in a certain wavelength range are stored at each of the plurality of parallel measuring points.

7. The method according to claim 6, wherein the plurality of parallel measuring points of one of the plurality of cross-directional profiles and the substantially continuous spectrum or the wavelength bands measured at each of the plurality of parallel measuring points are stored substantially simultaneously.

8. The method according to claim 6, wherein one of the plurality of cross-directional profiles substantially covers an entire width of the fibre web in the cross-direction instantaneously.

9. The method according to claim 1, wherein the method is used to monitor a coating of the fibre web.

10. The method according to claim 1, wherein the method is used to monitor a texture of the fibre web.

11. The method according to claim 1, wherein the method is used to monitor a roll, a suction roll, or roll coating.

12. The method according to claim 1, wherein the method is used to monitor a fibre web reel.

13. The method according to claim 1, wherein the at least one quality variable monitored by the method is a moisture level or a quantity of coating of the fibre web.

14. The method according to claim 1, wherein the electromagnetic radiation, which has been transmitted, reflected, or emitted by the fibre web, is measured substantially on the wavelengths of an infrared or near infrared range.

15. The method according to claim 1, wherein the electromagnetic radiation, which has been transmitted, reflected, or emitted by the fibre web, is measured substantially on the wavelengths of the visible range.

16. The method according to claim 1, wherein the process for manufacturing and/or finishing the fibre web is controlled, and/or a need for maintenance of the rotating/moving means and components used in the process for manufacturing and/or finishing the fibre web are evaluated, by a user or automatically.

* * * * *